(12) United States Patent
Carmeli et al.

(10) Patent No.: US 8,295,908 B2
(45) Date of Patent: Oct. 23, 2012

(54) DEVICE AND METHOD FOR OPENING VASCULAR OBSTRUCTIONS

(75) Inventors: Ran Carmeli, Rinatya (IL); Jonathan Einav, Raanana (IL); Itai Yonat, Tel-Aviv (IL)

(73) Assignee: Eyoca Medical Ltd., Tel-Aviv (IL)

( * ) Notice: Subject to any disclaimer, the term of this patent is extended or adjusted under 35 U.S.C. 154(b) by 919 days.

(21) Appl. No.: 11/914,095

(22) PCT Filed: May 9, 2006

(86) PCT No.: PCT/IL2006/000541
§ 371 (c)(1),
(2), (4) Date: Jul. 8, 2008

(87) PCT Pub. No.: WO2006/120674
PCT Pub. Date: Nov. 16, 2006

(65) Prior Publication Data
US 2009/0209900 A1 Aug. 20, 2009

(30) Foreign Application Priority Data

| May 11, 2005 | (IL) | 168568 |
| May 11, 2005 | (IL) | 168569 |
| Aug. 22, 2005 | (IL) | 170412 |

(51) Int. Cl.
*A61B 5/05* (2006.01)

(52) U.S. Cl. ........... 600/423; 600/407; 600/411; 604/22

(58) Field of Classification Search .................. 600/407, 600/411, 423; 601/2–4; 604/22
See application file for complete search history.

(56) References Cited

U.S. PATENT DOCUMENTS

| 3,570,476 | A | * | 3/1971 | Gregg | 601/2 |
| 5,234,451 | A | | 8/1993 | Osypka | |
| 5,569,179 | A | * | 10/1996 | Adrian | 604/22 |
| 5,628,719 | A | * | 5/1997 | Hastings et al. | 600/16 |
| 5,813,996 | A | | 9/1998 | St. Germain et al. | |

FOREIGN PATENT DOCUMENTS

| DE | 4215901 A1 | 8/1993 |
| DE | 10203371 A1 | 8/2003 |
| EP | 0934727 A | 8/1999 |
| WO | 9412234 A | 6/1994 |
| WO | 0000252 A | 1/2000 |

* cited by examiner

*Primary Examiner* — Tse Chen
*Assistant Examiner* — Peter Luong
(74) *Attorney, Agent, or Firm* — Richard S. Wesorick; Matthew M. Shaheen; Tarolli, Sundheim, Covell & Tummino LLP (57) ABSTRACT

The present invention is directed to a device and method for opening obstructed body internal passages and for sensing and characterizing tissues and substances being in contact with the device of the invention. In general, the device of the present invention comprises a catheter tube capable of inducing vibrations in a guidewire contained therein, wherein said vibrations of the guidewire are utilized for opening a passage through an occlusion. The in-vivo vibrations may be induced by means of a magnetic field actuating means (5) and a guidewire (2) comprising magnetic coupling means (3), or by means of transducers, which may be also used for the sensing.

21 Claims, 4 Drawing Sheets

DEVICE AND METHOD FOR OPENING VASCULAR OBSTRUCTIONS

FIELD OF THE INVENTION

The present invention relates to the field of minimal invasive catheterization. More particularly, the invention relates to a method and apparatus for opening and/or removing obstructions occluding body internal passages and for in vivo sensing of substance/tissue in body internal passages and body organs.

BACKGROUND OF THE INVENTION

Many vasocclusive events, such as heart attacks and strokes, are caused by plaque build-ups in arteries. As one specific example, atherosclerotic plaque is known to build-up in the walls of arteries in the human body. Such plaque build-up restricts circulation and often causes cardiovascular problems, especially when the build-up occurs in coronary arteries.

One common method for opening partially occluded body internal passages is to guide a medical device to the diseased site, where it is used to carry out the needed treatment. A guidewire is usually used for advancing a catheter device thereover via body internal passages towards the treatment site. Typically, the distal tip of the guidewire is introduced into the body of the treated subject via an incision and advanced therethrough towards the treatment site, thereby forming a path leading to the occluded site through said body internal passages. The catheter, or any other suitable treatment devices (e.g., balloon catheter, stent or rotational atherectomy device), may be then threaded over the guidewire and advanced through said internal passages using the guidewire as a rail.

Total or near-total occlusions in body internal passages can, partially or entirely, block the passage therethrough. For example, in patients who suffer from coronary CTO (chronic total occlusion), the successful performance of a Percutaneous Transluminal Coronary Angioplasty (PTCA) is a technical challenge. The factor that is most determinative of whether the practitioner can successfully perform PTCA on patients suffering from coronary CTO is his ability (or inability) to advance a suitable guidewire from a position proximal of the lesion to a position distal of the lesion while remaining inside the true vessel lumen (without performing perforation or dissection of the artery wall).

In some instances, such as where the occlusive matter is soft or where the body internal passage is partially occluded, the guidewire can easily be pushed through the occlusive matter itself, thereby allowing the guidewire to remain within the body internal passage. However, in other cases, such as when the body internal passage is totally occluded by hard plaque (e.g., calcified atherosclerotic plaque), the guidewire cannot cross the occlusion and may deviate to the side and penetrate through layers of the passage walls (e.g., the intima—inner layer of a vessel wall), thereby creating a neo-lumen therethrough (e.g., through the sub-intimal space—within the wall of the artery between the intima and media, or adventitia i.e. a dissection), or even completely exit said internal passage i.e. a perforation.

Several techniques are known for passing through an occluded internal passage, such as laser catheters (U.S. Pat. No. 6,673,064), ultra sonic catheters (U.S. Pat. No. 6,702,748), and tissue displacement or hinged expansion devices (U.S. Pat. No. 6,800,085). In all of those techniques the occlusion is opened by means of a catheter device equipped with operative means for occlusions opening. However, the prior art devices suffer from lack of flexibility and maneuverability due to the bulky structure of their catheter devices. Consequently, the treatment procedures which utilize these prior art devices are substantially different from conventional catheterization procedure workflow as commonly practiced in regular cases (non CTO cases).

The aforementioned prior art solutions also suffer from lack of ability to indicate to the practitioner in real time, i.e. while carrying out the procedure, whether he is navigating the treatment devices through the occlusion (true lumen) or if he is actually perforating or dissecting the body internal passage, e.g. the artery.

Other known procedures, such as described in U.S. Pat. No. 6,852,109, propose a method for forming a passage through the CTO by a guidewire having active Radio Frequency (RF) ablation tip, with Optical Coherence Reflectometry (OCR) capability for sensing the position of the tip. However this known type of guidewire is a special guidewire comprising a mechanism for transferring RF energy and a following catheter with fiber optics for the OCR capability. These restraints are relatively rigid and therefore diminish the flexibility of the device, which is an important feature for carrying out in vivo navigation. Thus, also this prior art device suffers from lack of flexibility, and the need to deviate from the conventional practice workflow of the practitioner.

Another solution used for determining whether an organic tissue is healthy or not is using IVUS (intravascular ultrasound), for example as described in U.S. Pat. Nos. 6,685,644 and 6,685,643, however lack of data due to poor transmission in this known method and calcified build-ups that cause "acoustic shadowing" yield poor results in determining tissue type and true lumen detection.

In still another solution used such as described in U.S. Pat. No. 5,908,395, a hand held vibrator is attached to the proximal side of a guide wire, or a catheter through which the guidewire is threaded.

The guidewire then conveys the proximal vibrations to its distal end, subject to the specific passage of the guidewire thru the arteries. If indeed these vibrations reach the distal end of the guidewire they may be efficient in penetrating and recanalization of CTOs (Chronical Total occlusions). However, there is a problem in that the vibrations may be absorbed before reaching the distal end. In addition, using an external hand held vibrator interferes with the standard operation of the guidewire, and limits the operator from conveniently controlling the guidewire by manually holding its proximal end, again causing the need to deviate from the conventional practice workflow of the practitioner.

There thus exists a need for devices and techniques for treating occluded body internal passages, for characterizing the tissue/substance the treatment device is in contact with and determining its location within and about the body internal passage, and for safely opening occlusions therein without damaging the occluded internal passage.

It is therefore an object of the present invention to provide a method and device for opening occluded body internal passages and/or body organs.

It is another object of the present invention to provide a method and device for safely navigating treatment means, such as a catheter device, to a treatment site through body internal passages.

It is a further object of the present invention to provide a method and device for in vivo characterizing the tissue and/or substance being in contact with a treatment device.

It is yet another object of the present invention to provide a catheter device capable of inducing vibrations in a guidewire contained therein.

Other objects and advantages of the invention will become apparent as the description proceeds.

SUMMARY OF THE INVENTION

The present invention is directed to a device and method for opening obstructed body internal passages and for sensing and characterizing tissues and substances being in contact with the device of the invention. In general, the device of the present invention comprises a catheter tube capable of inducing vibrations in a guidewire contained therein, wherein said vibrations of the guidewire are utilized for opening a passage through an occlusion.

More particularly, the present invention relates to a device and method for in vivo drilling in living tissue and/or finding the weak path in the said living tissue, in body internal passages and body organs, which may be utilized for opening a passage suitable for passing a treatment device (e.g., a stent, balloon) through an occluded body internal passage (e.g., blood vessel), such as in cases of total occlusion (Chronic Total Occlusion—CTO). The in vivo drilling is performed by means of a unique drilling guidewire, which aside from drilling through the occlusion can enable the operator to sense the tissue/substance being in contact with the drilling part of said drilling guidewire. The sensing of the tissue/substance contacting the drilling guidewire may be advantageously used to provide an indication as to whether the drilling guidewire properly operates in the occluded internal passage or whether it deviates therefrom and injures the passage wall. The path drilled and/or opened and/or re-canalized through the occluding matter enables the passage of a conventional guidewire through the occluded passage and thereby allows carrying out the conventional treatments applicable in such cases, such as, for example, by means of balloon catheters and stents.

The drilling according to this invention is carried out by means of rapid vibrations e.g., at a frequency of about several dozens of Hz, preferably in the region of 1-200 Hz, low amplitude vibrations e.g., with an amplitude of about a fraction of a mm, preferably in the region of 0.1 to 1 mm, that are directed in vivo to the occluding matter. The in vivo drilling device of the invention is designed to transfer the drilling energy with high efficiency into hard/calcified tissue, while keeping the efficiency low, when drilling into relatively soft tissues. The drilling vibrations are preferably limited to low amplitudes, resulting in a drilling scheme that transfers energy very efficiently into hard/calcified occlusions. At the same time, such drilling cannot transfer energy efficiently into soft tissues, such as the artery wall, thus lowering the risk of perforation or dissection thereof.

The in vivo drilling device of the present invention is preferably implemented by a guidewire comprising magnetic coupling means adapted for inducing axial vibrations therein by means of an alternating magnetic field. The magnetic coupling means may be implemented by a number of miniature magnetic elements (e.g., having a ring shape) radially attached to a section of a conventional guidewire or embedded within some segments of the guidewire itself. By applying rapid alternating/changing magnetic fields around the guidewire section that comprises said miniature magnets rapidly vibrate that guidewire section.

The alternating/changing magnetic field may be induced by alternating the frequency and magnitude (amplitude and direction) of the magnetic field. The magnetic field may be applied in vivo by a catheter device comprising a magnetic field actuating means mounted in section thereof corresponding to the location of the magnetic coupling means on the drilling guidewire. For example, the alternating magnetic field may be applied by a coil wound on (or in) a section of a catheter device (or embedded therein) comprising the drilling guidewire. An alternating magnetic field may be electrically applied by connecting the coil to an alternating electrical current source, which in effect vibrates the guidewire.

Additionally or alternatively, the alternating magnetic field is applied by vibratable fixed magnets mounted in a section of a catheter device comprising the drilling guidewire, and in a location corresponding to the location of the coupling magnets on the drilling guidewire or embedded in it. In particular, these vibratable fixed magnets can be attached to the catheter and have the shape of hollow cylinders, through which the guidewire passes. The vibration of the vibratable fixed magnets attached to the catheter may be achieved by means of electrically vibratable means, such as piezoelectric elements, which are attached to the magnets, wherein said electrically vibratable means can be powered by an external electrical power source. The power source may be of many forms, but preferably has a sinusoidal shaped output with alternating amplitude and frequency, thus providing vibrations of different characteristics.

The frequency of the vibrations may be changed in close loop in order to manually or automatically reach the resonance frequency or anti-resonance of the whole apparatus, thus gaining continuous leveling of the drilling energy.

The catheter device comprising the guidewire may include several separated electro-magnet coils. Each of those coils may be independently powered by an electrical current. Thus, by applying exciting current to each coil successively, (e.g., in a "wave" manner)—it is possible to achieve a relatively constant power over long range along the catheter/guidewire (e.g., as in linear stepping motor).

The electrical power (current and voltage vs. frequency) fed into the vibrating elements, can be analyzed to measure the overall apparatus magnetic impedance, and thereby provide an indication about the type of tissue/substance drilled, as described in Israel patent application No. 168569.

In addition, by continuously measuring the coil ohmic resistance (the instant ratio between the voltage develops on the coil and the current fed through the coil, one can deduct the ambient temperature surrounding the coils. This is based on the physical characteristic of the coil material, where its resistance depends on its temperature. This continuous measurement of the temperature, may also be used for providing an alert to the practitioner and/or for performing an automatic shut off of the active vibrations, whenever too high temperature is reached, and thereafter resuming the vibrations, when the ambient temperature surrounding the coils falls down to a safe level.

Alternatively or additionally, the vibration of the drilling guidewire may be achieved by other means, such as by providing a constant distally directed force on magnetic coupling means mounted on a distal end section of the drilling guidewire, and concurrently applying alternating proximally directed force, by externally (manually or mechanically) pulling the guidewire. In this way a longitudinal and possibly also a transverse vibrating mechanism is achieved.

Alternatively or additionally, the vibrations of the drilling guidewire may be achieved by clamping the guidewire within a catheter, while vibrating said catheter. More specifically, it may be excited, by using a catheter comprising at least two conduits, e.g., an inner conduit disposed within an outer conduit. The inner conduit, such as in a balloon catheter accurately matches the guidewire diameter. Magnets, preferably miniature in size and radial in shape are attached to the wall of the inner conduit, or are embedded therein. The outer conduit of the catheter is enwrapped or embedded in a coil, preferably several coils. The inner conduit is relatively free within the outer conduit, and hence by feeding an alternating current through the coils, an alternating magnetic force develops, vibrating the inner conduit of the catheter, and hence vibrating the guidewire clamped within the lumen of said inner conduit. Alternatively, the catheter device may be operated without the guidewire by using the distal end of the inner conduit as a drilling head.

Additionally or alternatively the inner magnets may be arranged non-radially, such that the generated vibrations may progress both, in longitudinal as well as in transverse directions.

Alternatively or additionally, the distal drilling tip of the guidewire is provided with bending piezon actuators, such that, by controlling the electrical current fed into the actuator, the guidewire tip can be vibrated and/or directed into a desired direction in vivo.

The present invention also provides means for in vivo sensing the tissue/substance with which the device of the invention is in contact or in proximity with by means of one or more acoustic transducers (e.g., Piezo electric transducers) and/or provides means for analyzing the magnetic impedance of one or more electric coils that are fed by an electrical alternating current. These transducers and or coils are held in proximity to living tissues affecting the acoustic and or magnetic impedance of the volume in the vicinity of the transducers and or coils. Changes in the acoustic and/or magnetic impedance results in changes in the voltage and current vs. frequency driving the transducers and/or coils. These changes can be measured by the driver of the transducers and/or coils, that may be remotely positioned away from the transducers and/or coils themselves, i.e. outside the body.

In one preferred embodiment of the invention the device is equipped with miniature magnets mounted and/or embedded near the distal tip of a guidewire. These magnets are activated when said guidewire is threaded through electrical coils fed with an electrical current. This guidewire, when threaded into body passageways or organs, can "feel" the different magnetic impedance surrounding its tip, as the guidewire is passed through said passageways and/or organ by the practitioner. In this embodiment, the driving unit of the coils is located remotely from the coils themselves.

The magnetic impedance of the coils is preferably measured at the driving unit end (proximal end) of the catheter. This measurement may be carried out by continuously measuring the electrical voltage over the coils and dividing the same by the value of the electrical current driving said coils. The magnetic impedance may be measured at different frequencies, thus providing a more comprehensive result of magnetic impedance at different frequencies. For this purpose the driving unit may be equipped with analog to digital converters and a processing unit for converting the values of the measured electrical voltage and driving current and computing the magnetic impedance by dividing the digital representation of the measured electrical voltage by the digital representation of the driving current.

The measured impedances may be used to characterize the tissue/substance that is in contact with, or in proximity to, the guidewire distal tip and thereby to provide clinical indications (e.g., to distinguish between plaque, blood, vessel walls or any other tissue that may be in the proximity of the tip of the guidewire), thus making it possible for the practitioner to distinguish between the plaque build-up inside the artery and the vessel walls (intima, media or adventitia).

In another embodiment of the invention the device of the invention is equipped with miniature acoustic transducers mounted at the distal tip of a guidewire. This guidewire, when threaded into body passageways, can "feel" the different acoustical impedance surrounding the transducers, as the guidewire is passed through the said passageways by the practitioner. In this embodiment, the driving unit of the transducers is located distantly from the transducers themselves. The acoustic impedance is preferably measured at the driving unit end (proximal end) of the guidewire. The measured impedances may be used to characterize the tissue/substance being in contact with the guidewire distal tip and thereby to provide clinical indications (e.g., allow to distinguish between plaque, blood, vessel walls or any other tissue that may be in the proximity of the tip of the guidewire), thus making it possible for the practitioner to distinguish between the plaque build-up inside the artery and the vessel walls (media).

Additionally or alternatively, the device of the invention includes electrically vibratable means, such as an ultrasound transducer, embedded in the distal end of the drilling guidewire and/or in the catheter distal end, thereby allowing vibrating the distal end of the device at an ultrasonic frequency (controlled and regulated from a control unit connected to the proximal end of the unit in vitro) for drilling through the occlusion. The electrically vibratable means preferably comprises a micro piezoelectric device capable of efficiently transferring energy to hard/calcified tissues and thus allows destruction of plaque rather then of the passageway wall.

The drilling effect of the device of the present invention is achieved by two main mechanisms: i) the direct rapid mechanical vibrations applied into the occlusion, or ii) by cavitation effect, in which the ultrasonic waves in the blood produce tiny bubbles, forming a fractal structure and radiating sound by themselves. The cavitation field that is being produced by a radially symmetric sound field burst of approximately 23 kHz onto the occlusion at high energy, thus damaging and/or breaking up the plaque.

The catheter device of the invention may be implemented using a low diameter catheter tube which includes a magnetic guidewire centering means surrounding the guidewire. This magnetic guidewire centering means uses unidirectional magnetic forces that force a guidewire comprising a magnetic element to float inside the catheter due to repulsion of magnetic forces evolving between said magnetic element and said magnetic guidewire centering means, thus stabilizing the guidewire (ensuring the guidewire will vibrate in a controlled direction and will not deviate in undesirable directions) thereby reducing friction and improving guidewire rotational movement abilities. This magnetic centering means may be either passive, i.e. comprising fixed magnets, or active, i.e. comprising a combination of fixed magnets and electromagnetic coil.

The device of the invention may further include a lumen for debris aspiration, and it may be further adapted to allow injection of fluids via the guidewire lumen, such as contrast media and/or cooled saline for temperature control.

The invention also provides a means for deflecting the driller tip into a desired in vivo direction thereby imparting additional maneuverability to the distal tip of the guidewire, when passing through complicated artery morphologies.

The catheter device of the invention may be equipped with a thermo-sensor mounted in the distal end of the catheter that is used to communicate temperature readings to the practitioner either via wires or wirelessly, from the distal end of the catheter to the proximal end.

The proximal end of the catheter device of the invention may be bifurcated to provide a first entrance for the drilling/sensing guidewire and an entrance for saline/contrast media or other fluid, the debris aspiration tube, the ultrasound transducer power cords and the thermo-sensor power/reading cords, if any.

The present invention also provides a method for opening occluded body passageways by means of a drilling guidewire, which may be a conventional guidewire that is slightly modified and which may be operated (upon physician selection) in an active mode (electrically powered) as a driller held by the catheter surrounding the guidewire near its distal end. Thereby, the physician can advance the guidewire as far as possible towards the occlusion while the device is in a passive mode, and upon reaching an occluded section switching the device into an active mode, thereby initiating a drilling process to allow further advancing the guidewire all the way to the distal end of the occlusion, and thereafter to treat the occluded passageways using conventional procedures, such as by means of balloon catheters and/or stents.

BRIEF DESCRIPTION OF THE DRAWINGS

The present invention is illustrated by way of example in the accompanying drawings, in which similar references consistently indicate similar elements and in which.

DETAILED DESCRIPTION OF PREFERRED EMBODIMENTS

Figure 1A:
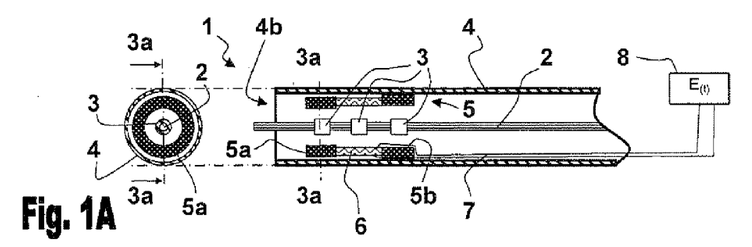
FIG. 1A shows a longitudinal and a cross-sectional views of a catheter device of the invention for opening occluded passageways by means of a vibrated magnetic field.

FIG. 1 shows longitudinal and cross-sectional views of a device 1 designed for in vivo generating and transferring mechanical vibrations. The device 1 comprises a catheter tube 4 and a drilling guidewire 2 passing therethrough. Drilling guidewire 2 comprises miniature magnets 3 radially attached thereto near its distal tip. Catheter tube 4, comprising guidewire 2, comprises magnetic field inducing means 5 attached to the inner wall of catheter tube 4 near its distal end opening 4b. Magnetic field inducing means 5 may also be embedded in the wall of catheter tube 4 (not shown). In this preferred embodiment magnetic field inducing means 5 are implemented by a structure comprising fixed magnets, 5a and 5b, and vibratable (e.g., piezoelectric) elements 6, attaching the fixed magnets. Vibratable elements 6 are supplied with electrical power $E_{(t)}$ provided by electrical power source 8 via electrical wiring 7. Drilling guidewire 2 comprises magnetic coupling means implemented by miniature magnets 3 mounted near a distal end portion thereof.

Fixed magnets, 5a and 5b, and vibratable elements 6 are preferably hollow cylindrical elements configured to allow passage of a guidewire therethrough. Alternatively they may be embedded within guidewire 2. When operated in a drilling mode, an alternating electrical signal is supplied to vibratable elements 6 which in turn vibrate fixed magnets 5a and 5b, thereby inducing a vibrating magnetic field in the proximal end portion of catheter tube 4. Miniature magnets 3 are affixed near a distal end section of guidewire 2 such that when said distal end section of guidewire 2 is positioned within the structure comprising fixed magnets, 5a and 5b, and vibratable (e.g., piezoelectric) elements 6, a distal end portion of guidewire 2 protrudes outwardly via the distal end opening of catheter tube 4.

The structure comprising fixed magnets, 5a and 5b, and vibratable elements 6, connecting said fixed magnets may be attached to the inner wall of catheter tube 4 via magnet 5b, such that magnet 5a connected thereto via vibratable element 6 is maintained in the interior of the catheter in a more or less floating state, as exemplified in FIG. 1A. Alternatively, vibratable elements 6 may be attached to the outer wall of catheter tube 4, or be embedded therein (not shown). In a similar fashion additional magnets 5a may be attached by means of vibratable elements 6a, 6b and 6c, connected therebetween, to provide a structure of "floating" magnets 5a connected to magnet 5b, which is affixed to the inner wall of catheter tube 4, as exemplified in FIG. 1B. Similarly, said structure containing "floating" magnets 5a is free to vibrate in the guidewire lumen of catheter tube 4.

Guidewire 2 may be a conventional guidewire such as the Cordis Wizdom guidewire (Johnson & Johnson, USA), or more preferably may be a guidewire having medium distal stiffness, specially designed for treatment of CTOs such as the Pilot 50 manufactured by Guidant, USA. Miniature magnets 3, can be manufactured from rare earth materials such as NdFb series, preferably from NdFeB grade 42 or higher, and they are preferably in the shape of miniature hollow cylinders attached to the guidewire 2, as shown in the cross-sectional view in FIG. 1A, or are embedded within the guidewire (not shown). The outer diameter of the magnets 3 should be configured according to the diameter of guidewire 2, for example, if the diameter of guidewire 2 is about 0.36 mm (14 mils), then the outer diameter of miniature magnets 3 may generally be in the range of 0.5 to 1.0 mm, preferably about 0.7 mm, while their inner diameter should match the guidewire diameter or will be reduced down to zero in the case they are embedded in the wire. The thickness of the miniature magnets 3 can vary and reach several mm, all in accordance to the guidewire they are attached to and or embedded within. For example, the length of miniature magnets 3 may generally be in the range of 1.0 to 5.0 mm, preferably about 2.5-3.0 mm.

The distal end portion of guidewire 2 is preferably made of a material that is softer or less stiff, in relation to the other portions thereof in order to allow it to collapse and in this way to avoid any possible damage, such as perforation or dissection to the arteries wall. Miniature magnets 3 are preferably affixed on a distal section of guidewire 2, near its distal end portion. While in the above examples, and in the figures, miniature magnets 3 and guidewire 2 are concentric, and the intervals between miniature magnets 3 are of equal length, the invention may also advantageously utilize different configurations. For example, miniature magnets 3 may be mounted on guidewire 2 in a non-concentric form and the interval between miniature magnets 3 may be of different lengths.

Similarly, the geometrical dimensions of fixed magnets, 5a and 5b, and vibratable elements 6 should be adjusted according to the inner radius of catheter tube 4. For example, if the inner diameter of catheter tube 4 is about 1.0 mm, then the outer diameter of fixed magnets, 5a and 5b, may generally be in the range of 0.7 to 0.9 mm, preferably about 0.8 mm. Fixed magnets, 5a and 5b, can be manufactured from rare earth materials such as NdFeB series, preferably from NdFeB grade 42 or higher, and vibratable elements 6 is preferably a type of piezoelectric element, such as manufactured by APC.

By applying voltage of the order of several dozens of Volts to the opposite ends of the piezoelectric element, said element bends and straightens at an amplitude of a fraction of a mm, hence changing the magnetic field surrounding the magnets attached to guidewire 2. This change in the magnetic field causes evolution of a magnetic force of the order of up to several grams.

Figures 1B, 1C:
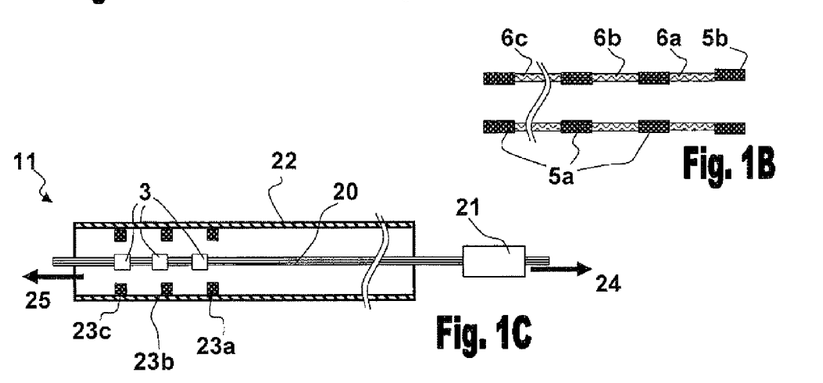
FIG. 1B illustrates a possible arrangements of magnets and electrically vibratable means.
FIG. 1C illustrates a catheter device of the invention for opening occluded passageways by mechanically induced vibrations and magnetic attraction forces.

FIG. 1C is a longitudinal view of a device 11 of the invention in which the proximal end of guidewire 20 is held by mechanical means 21, capable of repeatedly applying rapid longitudinal pulling forces (designated by arrow 24) thereto. Mechanical means 21 may be implemented by several methods, for example by connecting guidewire 20 to an external vibratable element, such a piezoelectric transducer, activated by a suitable electrical powering signal. Catheter tube 22 includes a series of fixed magnets 23a, 23b, 23c, . . . , affixed to (or alternatively embedded in, not shown) the inner wall of catheter tube 22. Internal magnets 23a, 23b, 23c, . . . , are preferably hollow cylindrical magnets configured to apply distally pulling forces (designated by arrow 25—pulling towards the distal end of the guidewire) on miniature magnet 3 affixed to (or embedded in, not shown) guidewire 20. External mechanical means 21 applies repeated rapid pulling force (24) which due to the distal attraction applied by fixed magnets 23a, 23b, 23c, . . . , results in rapid longitudinal vibrations of the distal tip of the guidewire 20.

Fixed magnets 23a, 23b, 23c, . . . , can be manufactured from rare earth materials such as NdFeB, preferably from NdFeB grade 42 or higher. The inner outer diameter of fixed magnets 23a, 23b, 23c, . . . , should be set according to the inner diameter of catheter tube 22. For example, if the inner diameter of catheter device is about 1.0 mm, then the outer diameter of fixed magnets, 23a, 23b, 23c, . . . , may generally be in the range of 0.7 to 0.9 mm, preferably about 0.8 mm.

Figures 1D, 2A:
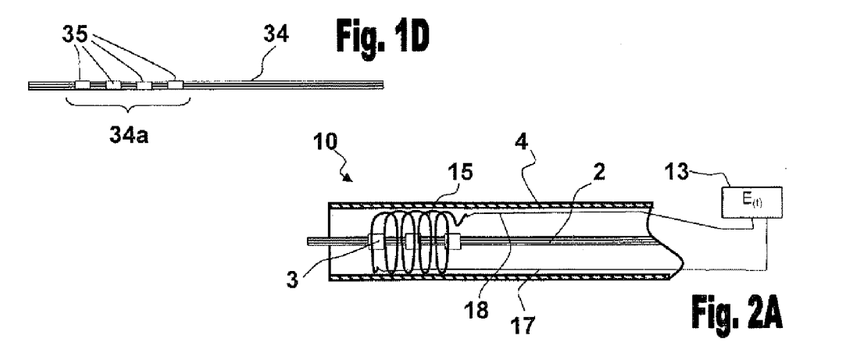
FIG. 1D shows a possible guidewire structure of the invention having an embedded ferromagnetic section.
FIG. 2A illustrates a catheter device of the invention for opening occluded passageways by means of a magnetic field induced by a coil.

FIG. 1D shows a possible preferred embodiment of a guidewire 34, which is equipped with a segment 34a comprising ferromagnetic and/or magnetic portions 35 embedded therein, thereby creating a ferromagnetic and/or magnetic segment 34a, which diameter is not larger, or only slightly larger, than the original diameter of the guidewire 34. This ferromagnetic and/or magnetic segment 34a, when inserted into a magnetic field gradient is subject to magnetic forces. Of course, the number of ferromagnetic and/or magnetic portions 35 provided in guidewire 34 may be different than that exemplified in FIG. 1D.

FIG. 2A illustrates a catheter device 10 of the invention which is capable of generating an alternating magnetic field in a lumen thereof by means of an electromagnetic coil 15 wrapped on the inner wall of catheter tube 4. Alternatively, coil 15 may be externally wrapped on the outer surface of catheter tube 4, or embedded inside the catheter wall. Coil 15 is preferably located near the distal end opening of catheter tube 4, and it is activated by an electrical current supplied thereto by means of electrical wires 17 and 18 electrically connecting it to electrical driving unit 13. Coil 15 is preferably a wrapped wire made from a flexible and electrically conducting material, preferably from copper, and coated with a type of a bio-compatible material, preferably parylene. The diameter of said wrapped wire may be in the range of 0.02 to 0.25 mm, preferably about 0.1 mm. The number of turns of coil 15 may vary according to the implementation specific requirements. For example, in one possible embodiment of the invention the number of turns of coil 15 may be in the range of 30 to 150 turns. The axial length of coil 15 should be adjusted according to the length of the section of guidewire 2 comprising the miniature magnets e.g., about 10 mm.

Figure 2B:
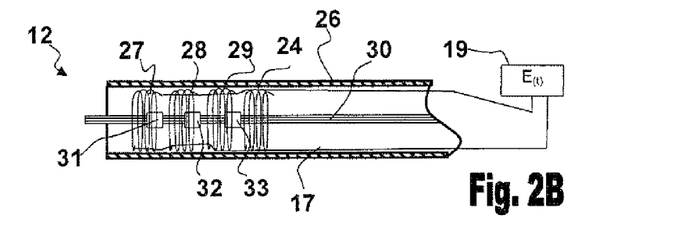
FIG. 2B illustrates a catheter device of the invention for opening occluded passageways by means of a magnetic field induced by a plurality of coils.

FIG. 2B illustrates a catheter device 12 of the invention comprising catheter tube 26 equipped with several coils 27, 28, 29, 24, positioned near its distal end and arranged in a Helmholtz like configuration. Coils 27, 28, 29, 24, may be wrapped on the inner wall of catheter tube 26, on its outer surface, or alternatively embedded inside the catheter wall. Guidewire 30 passing in the lumen of catheter tube 26 comprises miniature magnets 31, 32, 33, . . . , attached thereto. The location of the coils 27, 28, 29, 24, and magnets 31, 32, 33, . . . , in catheter device 12 is preferably configured to provide segments of adjacently located pairs of coils together with a magnet. For example, coils 27 and 28 may surround magnet 31, coils 28 and 29 may surrounds magnet 32, etc. Upon excitation of the coil pairs a gradient of magnetic field is generated inbetween the coils. When this gradient is generated near the fixed magnets 31, 32 and 33 a magnetic force is excited. In the embodiment shown in FIG. 2B, the current in coils 27 and 29 may be in a clockwise direction, while the current in coils 28 and 24 may be in a counterclockwise direction. The magnets, may then be positioned such that the north poles of magnets 31 and 33 are at the distal side of the magnets, while the north pole of magnet 32 is at the proximal side thereof. Using such an arrangement achieves a multiplication of the magnetic force operating on a single magnet. The multiplication factor is determined by the number of coil/magnet segments. It goes without saying that a different number of coil/magnet segments, other than the three segments shown in the FIG. 2B, may be employed.

For example, an apparatus including 4 coils (3 segments), each having 34 turns, which are being fed with a 1 A electrical current, can produce a force of 3 grams when measured on 3 miniature magnets, the length of which is about 3 mm, and having an outer diameter of about 0.8 mm and an inner diameter of about 0.4 mm.

Figure 2C:
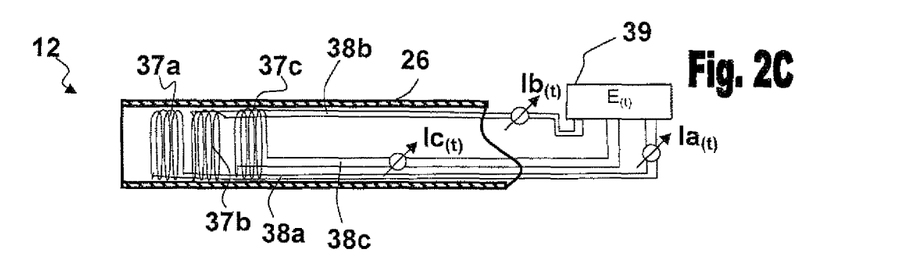
FIG. 2C illustrates a catheter device of the invention for opening occluded passageways by means of a magnetic field induced by a plurality of coils separately energized by a power source.
Figure 2D:
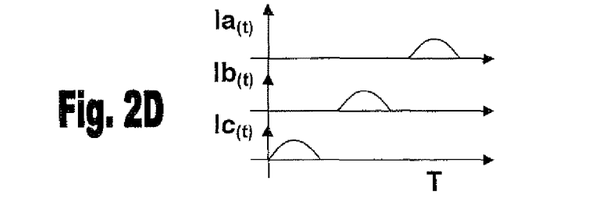
FIG. 2D shows a possible electrical activation scheme of the separate coils arrangement shown in FIG. 2C.

FIGS. 2C and 2D demonstrates an operation/excitation scheme of a catheter device 12 in which the coils 37a, 37b. 37c, . . . , provided in the catheter tube 26 are separately powered via respective wires 38a, 38b, 38c, . . . , electrically connecting said coils to an external power source 39, such that each coil may be operated independently. While it is possible to operate/excite all of the coils 37a, 37b. 37c, . . . , that surround the guidewire 30 (not shown in FIG. 2C) in phase (meaning the powering electrical current is fed to all coils simultaneously) it is also possible to excite the coils in series one after the other, as exemplified in FIG. 2D.

FIG. 2D graphically illustrates the currents $Ia_{(t)}$, $Ib_{(t)}$, $Ic_{(t)}$, . . . , supplied to coils 37a, 37b, 37c, . . . , respectively in such a possible activation scheme. This activation scheme provides the coils with "wave" like current. The magnetic field is consequently developed in a wave like manner—providing a relatively high duration magnetic field that propagates along the catheter tube 26. Inserting a guidewire 30 (such as shown in FIG. 2B) results in an apparatus that provides relatively constant magnetic force along relatively long range along the catheter/guidewire axis.

Additionally, by measuring the coil ohmic resistance (the instant ratio between the voltage developed on the coil and the current fed through the coil), one can deduce the temperature of the ambient surrounding the coils.

Advantageously, coils 37a, 37b, 37c, . . . , may be designed such that the direction of the activation currents of adjacent coils (e.g., $Ia_{(t)}$ and $Ib_{(t)}$) are of opposing directions in order to generate magnetic field gradients in the lumen catheter tube 26. The distances between coils 37a, 37b, 37c, . . . , may be of different lengths in order to provide varying distances between the magnetic field gradients.

Clearly, other waveforms different than those shown in FIG. 2D, may be fed into the coils, where the number of coils may again differ from the 3 coils shown in FIG. 1A.

Figure 3A:
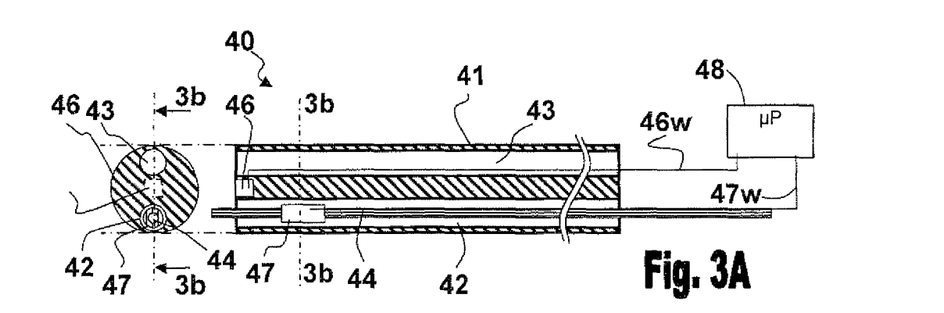
FIG. 3A shows a longitudinal and a cross-sectional views of a catheter device of the invention for opening occluded passageways by means of an electrical vibratable element.

FIG. 3A shows longitudinal and cross-sectional views of a catheter device 40 comprising a vibratable guidewire 44 designed for in vivo generating and transferring of acoustical (and/or other type of) vibrations. Guidewire 44 passing inside guidewire lumen 42, comprises an ultrasonic (or another type of) vibrating element 47 that may be used for in vivo inducing vibrations (e.g., acoustic vibrations) and/or for sensing and characterizing the substance/tissue that is in proximity to the distal end of the guidewire device 44. Guidewire lumen 42 may be also used for injection of liquid, such as cold saline or contrast media. Catheter tube 41 further comprises a debris aspiration lumen 43 and a thermo-sensor 46. At the proximal end of catheter tube 41, there are shown power wires 47w, of the vibrating element 47, and wires 46w connecting to the thermo-sensor 46. Of course, wires 46w are absent when the device according to the invention does not include a thermo-sensor. Wires 46w and 47w are connected to a control unit 48 capable of inputting thermal readings from thermo-sensor 46, providing powering signals to vibrating element 47, and inputting and analyzing signals produced by vibrating element 47.

Figure 3B:
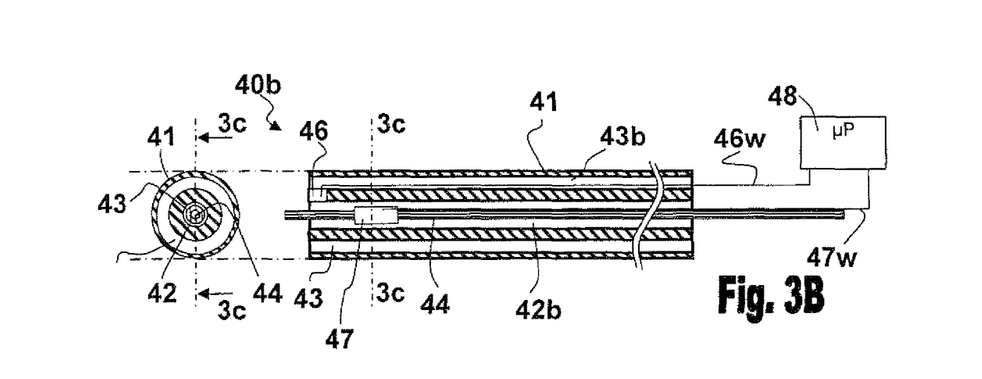
FIG. 3B shows a longitudinal and a cross-sectional views of another embodiment of the catheter device of the invention for opening occluded passageways by means of an electrical vibratable element.

FIG. 3B shows longitudinal and cross-sectional views of a catheter device 40b comprising a vibratable guidewire 44 designed for in vivo generating and transferring of acoustical and or other type of vibrations. The operation of catheter device 40b is similar to that of catheter device 40. The structure of catheter device 40b is, however, different in that the guidewire lumen 42b is concentrically located in the debris aspiration lumen 43b.

Figure 4A:
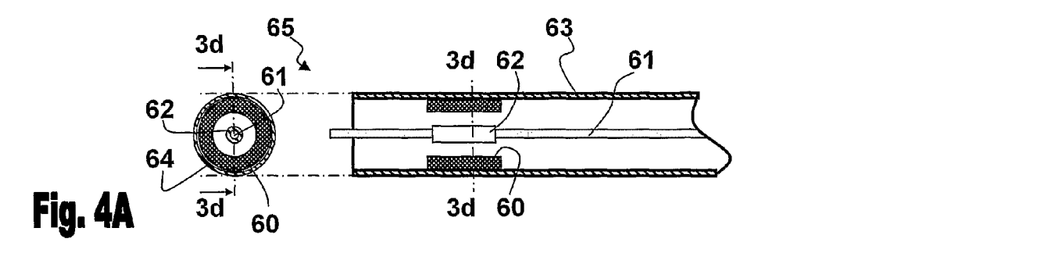
FIG. 4A illustrates a catheter device of the invention capable of centering a guidewire passing therein by means of fixed magnets.
Figure 4B:
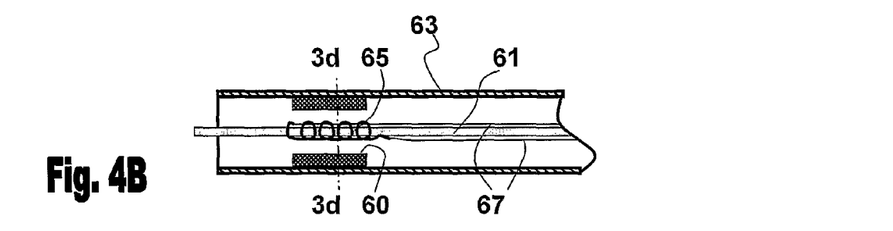
FIG. 4B illustrates a catheter device of the invention capable of centering a guidewire passing therein by means of a fixed magnet and an electromagnetic coil.

FIG. 4A illustrates a possible arrangement for a catheter device 65 capable of centering a guidewire 61 passing therethrough by means of fixed magnets, 60 and 62. Fixed magnet 60 is preferably a hollow cylindrical magnet attached to the inner wall of catheter tube 63 (or embedded in it, not shown), such that guidewire 61 can be freely moved longitudinally therethrough. Fixed magnet 62 is affixed to guidewire 61 at a location corresponding to the location of fixed magnet 62 in catheter tube 63. Fixed magnets 60 and 62 are designed such that repulsion forces caused due to their opposite magnetic polarities centers guidewire 61 inside catheter tube 63 when positioned therein in its operative state, as exemplified in FIG. 4A. In similar way, in FIG. 4B guidewire 61 is centered inside catheter tube 63 by means of electromagnetic coil 65. Coil 65 may be activated once guidewire 61 is positioned in an operative state in catheter tube 63 by supplying it electrical current via conducting wires electrically connected to it.

Figures 5A, 5B, 5C:
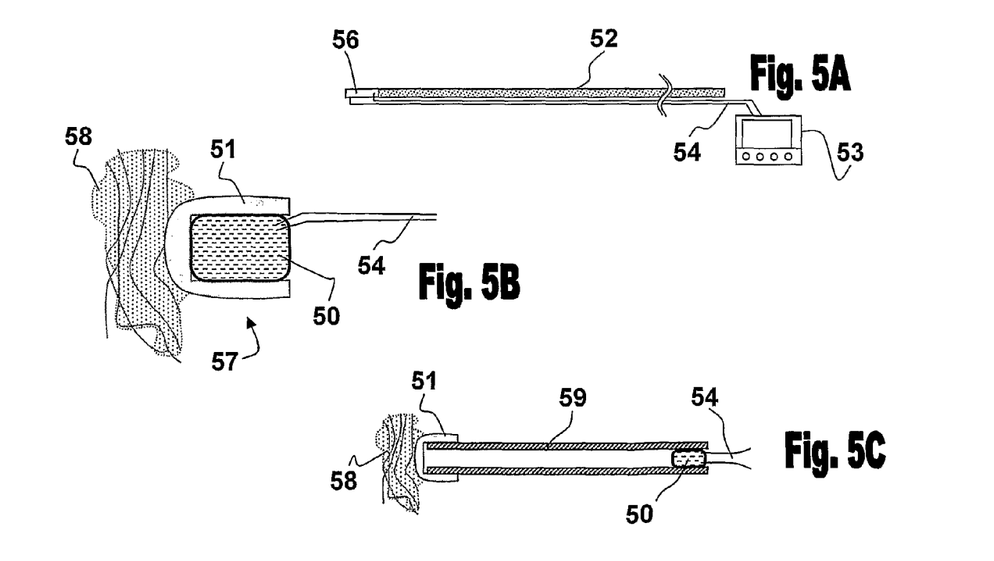
FIG. 5A illustrates a guidewire of the invention comprising an acoustic impedance sensing means.
FIG. 5B illustrates a possible acoustic head arrangement of the invention.
FIG. 5C illustrates a possible structure of an acoustic transducer comprising a waveguide.

FIG. 5A shows a conventional guidewire 52 comprising one or more miniature acoustic and/or other transducers 56 which are fed with electrical power provided by electronic unit driver 53 electrically connected thereto by means of electrical wires 54. Electronic unit driver 53 is advantageously designed to provide various electrical supply signals, in particular it may be able to supply direct current (DC) and alternating current (AC) in high frequencies.

FIG. 5B shows a preferred embodiment of the acoustic or other transducer 57 of guidewire 52. Acoustic or other transducer 57 comprises an active part 50, such as a piezoelectric module, which is fed via wires 54 electrically attached thereto. Active part 50 is packed in an acoustic\vibrating head 51. Head 51 can provide readings that may be used to characterize tissue/substance 58 which it is acoustically or physically touching, and/or which is in its proximity. The design and construction of acoustic head 51 may vary from one embodiment to another, depending on the tissue/substance 58 in proximity thereto.

FIG. 5C shows another embodiment of a transducer (e.g., acoustic transducer) of the invention in which the active part 50 (that may be a piezoelectric transducer) is coupled to head 51 (e.g., acoustic head), via a waveguide 59 (e.g., acoustic waveguide). Conducting wires 54 are used to provide electrical supply to active part 50, and to output signals read from active part 50 that may be used to characterize tissue/substance 58 with which it is in contact, or in its proximity. It should be mentioned that waveguide 59, may carry both longitudinal waves, and/or transverse waves or both, and it may be built either in hollow configuration or solid one, with different lengths as implied by the specific implementation of this embodiment. Guidewire 52 may be a conventional cardiac coronary guidewire as commonly used in coronary catheterization procedures.

When the guidewire reaches a lesion difficult to pass, the sensing tip is activated and transmits acoustic or vibrating energy into the problematic lesion. The impedance of that lesion is relative to the type of occlusion reached. Thus the practitioner can determine whether he reached a healthy part of the artery (touching the vessel wall for instance) or a diseased portion, i.e. a calcified/fibrotic and/or other type of occlusion.

Figure 5D:
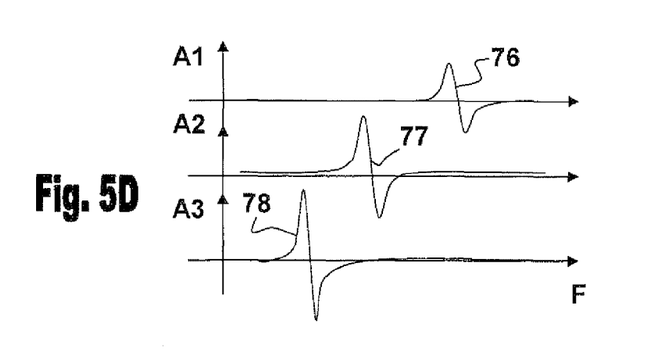
FIG. 5D exemplifies various signals that may be obtained via acoustic impedance sensing means.

The interpretation of the occlusion reached is done by remotely analyzing the acoustic impedance of the material that is in proximity to the guidewire tip. A schematic reading for that acoustic impedance is shown roughly in FIG. 5D. Items 76, 77 and 78 represent acoustic impedances of different substances/tissues that were measured in proximity to the guidewire tip.

Figure 5E:
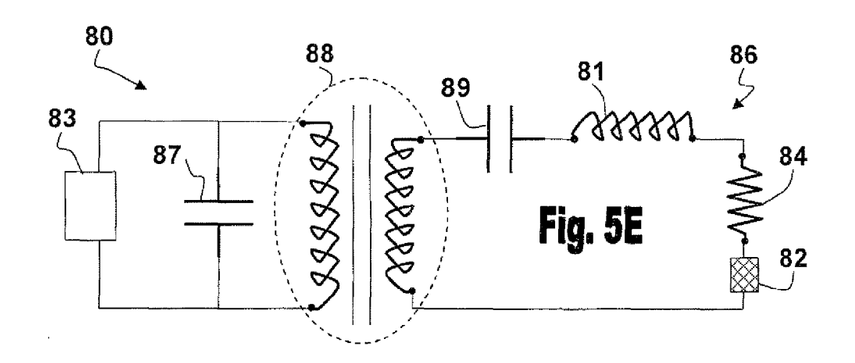
FIG. 5E schematically exemplifies the operation of an acoustic transducer of the invention.

FIG. 5E illustrates the physical mechanism of the acoustic transducer of the invention. In any embodiment used, and under certain physical estimations, the behavior of the acoustic transducer, and its interaction with the substance/tissue it is in proximity with is as illustrated in FIG. 5E.

The left side, designated by numeral 60, is the electrical equivalent of the acoustic transducer. It comprises an electronic unit driver 63 connected to the acoustic transducer. The electrical characteristics of the acoustic transducer are described by an LC circuit, 67 and left part of transformer 68.

The transformation of the electrical energy into the mechanical movement/energy of the transducer (that then creates acoustic energy) is effected by transformer coupling 68. The right side of transformer 68 provides the energy to activate the acoustic transducer. In the case of most acoustic transducers, and specifically in piezoelectric type transducers, the energy is fed into them is converted into mechanical movements. Parts 69 and 61 represent the construction of the transducer itself.

A capacitor 89, connected in series with inductor 81, provides a simple apparatus, with a single resonance frequency. This representation can then be used to represent an acoustic transducer up to the first resonance (but it gives a simple illustration to the physical mechanism). In the acoustic domain, the velocity and the force which represent the mechanical characteristics of the transducer correspond to the current and voltage, respectively of capacitor 89 and inductor 81.

Since there is always loss of energy, the device includes resistor 84. The interaction of the acoustic transducer with the tissue sensed is represented by 82.

When the transducer apparatus is operated, it receives the activating energy from the electronic unit driver 83, and in response it mechanically moves parts 89 and 81 which create an acoustic energy, some of which is transferred to resistor 84, while the rest penetrates into the tissue 82.

The "load" induced by the tissue (the equivalent acoustic load of 82) influences the behavior of the system. It actually changes the relationship between the velocity and power of the acoustic transducer, which is correlated to the voltage and current of the driver.

It is then possible to measure the electrical impedance (ratio between voltage and current) at the left side of the apparatus 80, and estimate the acoustic impedance of the right side 86.

Again, the acoustic impedance depends on the mechanical characteristics of the acoustic transducer (parts 89 and 81), the efficiency of the acoustic process 84 and the acoustic characteristics of the tissue 82 which is in proximity to the transducer. Thus, by estimating the acoustic impedance of the apparatus, it is possible to derive the acoustic characteristics of the tissue to sense.

It should also be mentioned that other equivalent schemes for apparatus containing acoustical transducers may be used. Some of those alternative schemes may be found in the existing technical literature, for example in "Introduction to Theory and Design of Sonar Transducer", written by Oscar Bryan Wilson and published by Peninsula Publishing, Los Altos Calif., USA-1985.

Figure 6:
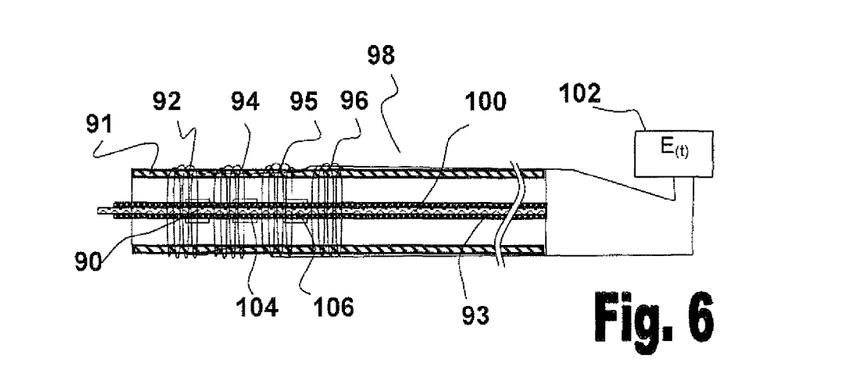
FIG. 6 illustrates a longitudinal view of another embodiment of the catheter device of the invention which is comprised of an outer conduit comprising an inner conduit, wherein a guidewire is threaded through the lumen of the inner conduit which is surrounded by miniature magnets, and wherein coils are wrapped around the outer conduit of the catheter.

FIG. 6 shows another embodiment of the invention comprising a catheter device capable of vibrating a conventional guidewire passing therein. In this embodiment the catheter device 98 comprises at least two conduits: An outer conduit 91 and an inner conduit 93. Guidewire 100 is threaded through the lumen of the inner conduit 93, and a distal end portion thereof emerges via the distal end opening of outer conduit 91 of catheter device 98.

Several magnets 90, 104 and 106 are attached around the outer surface of inner conduit 93. The length of magnets 90, 104 and 106 may be in the range of 1.0 to 5.0 mm. Magnets 90, 104 and 106 may have a hollow cylindrical shape having an outer diameter in the range of 0.5 to 1.5 mm, and an inner diameter that matches the outer diameter of conduit 93. Coils 92, 94, 95 and 96, wrapped over the outer surface of outer conduit 91, are made from a type of electrically conducting material, preferably from a copper wire coated with a biocompatible material, preferably parylene, wherein the wire diameter is in the range of 0.05 to 0.25 mm.

The diameter of the inner conduit 93 of catheter 98 is designed to tightly fit over the outer surface of guidewire 100, thereby forcing guidewire 100 to axially move distally and proximally in a longitudinal direction. The diameter of inner conduit 93 may generally be in the range of 0.4 to 0.6 mm.

When activating coils 92, 94, 95 and 96 via an external driver 102, a magnetic field is induced, which in effect introduce a magnetic force acting on magnets 90, 104 and 106. Alternating the current fed into these coils results in alternating the magnetic force acting on the magnets, which in turn results in vibrations of inner conduit 93 relative to outer conduit 91 of catheter 98. Since the inner conduit 93 clamps guidewire 100, guidewire 100 is forced to vibrate as well.

While in the example shown in FIG. 6 coils 92, 94, 95 and 96, are wrapped externally (on the outer surface of outer conduit 91), they may as well be wrapped internally on the inner wall of outer conduit 91, or embedded in its wall. Similarly, magnets 90, 104 and 106 may be embedded into the wall of inner conduit 93.

All of the abovementioned parameters are given by way of example only, and may be changed in accordance with the differing requirements of the various embodiments of the present invention. Thus, the abovementioned parameters should not be construed as limiting the scope of the present invention in any way. In addition, it is to be appreciated that the different tubes, wires, magnets, and other members, described hereinabove may be constructed in different shapes (e.g. having oval, square etc. form in plan view) and sizes differing from those exemplified in the preceding description.

The above examples and description have of course been provided only for the purpose of illustration, and are not intended to limit the invention in any way. As will be appreciated by the skilled person, the invention can be carried out in a great variety of ways, employing more than one technique from those described above, all without exceeding the scope of the invention.

The invention claimed is:

1. A device for inducing in-vivo vibrations in a body passageway or an organ, comprising:
   a catheter tube comprising a conduit and at least one electromagnetic coil attached to the conduit, the at least one electromagnetic coil being activated with an alternating electrical current to create an alternating magnetic field within at least one section of the conduit; and
   a guidewire positioned in the conduit, the guidewire comprising a distal end portion, an adjacent proximal portion, and at least one permanent magnet fixedly attached to the adjacent proximal portion,
   the at least one permanent magnet oscillating longitudinally in response to the alternating magnetic field when the at least one permanent magnet is positioned in the at least one section of the conduit, the longitudinal oscillations of the at least one permanent magnet producing longitudinal oscillations in the distal end portion of the guidewire.

2. The device according to claim 1, wherein the at least one permanent magnet is embedded in the guidewire.

3. The device according to claim 1, wherein the at least one permanent magnet is mounted on a surface of the guidewire.

4. The device according to claim 1, wherein the at least one permanent magnet is manufactured from NdFeB rare earth alloy.

5. The device according to claim 1, wherein the at least one electromagnetic coil is made from at least one turn of electrically conductive wire.

6. The device according to claim 1, wherein the alternating magnetic field is induced by controlling at least one of the frequency and amplitude of the alternating electrical current.

7. The device according to claim 1, wherein the at least one electromagnetic coil is at least one of embedded in the catheter tube and mounted on a surface of the catheter tube such that a section of the guidewire passes through the at least one electromagnetic coil.

8. The device according to claim 1, wherein the at least one electromagnetic coil is electrically connected to an electrical power source by means of electrical wires that extend along the length of the catheter tube.

9. The device according to claim 1, wherein the at least one electromagnetic coil comprises a plurality of electromagnetic coils electrically connected to an electrical power source by means of electrical wires.

10. The device according to claim 9, wherein the at least one permanent magnet comprises a plurality of permanent magnets, the directions of the electrical currents in adjacent electromagnetic coils flowing in opposing directions, and the polarities of adjacent permanent magnets opposing each other.

11. The device according to claim 9, wherein the electromagnetic coils are powered independently by the electrical power source.

12. The device according to claim 8, wherein the electrical power source comprises means capable of measuring the ohmic resistance of the electromagnetic coils in order to determine the temperature of the electromagnetic coils.

13. The device according to claim 1, wherein the at least one permanent magnet is shaped in the form of a hollow cylinder.

14. The device according to claim 1, wherein the distal end portion of the guidewire has a stiffness that is different than a stiffness of the adjacent proximal section of the guidewire to which the at least one permanent magnet is attached.

15. A device for inducing in-vivo vibrations at a treatment site in a body, comprising:

a guidewire for insertion into the body via an incision, the guidewire comprising a distal end portion for navigating a body passageway to reach the treatment site, the distal end portion having a stiffness that is lower than that of an adjacent proximal portion of the guidewire; and a catheter tube positioned over the guidewire in the body passageway, wherein the catheter tube comprises at least one electromagnetic coil attached to the catheter tube, the at least one electromagnetic coil being activated with an alternating electrical current to create an alternating magnetic field within at least one section of the catheter tube, and wherein the guidewire further comprises at least one permanent magnet fixedly attached to the guidewire proximal to the distal end portion, the at least one permanent magnet oscillating longitudinally in response to the alternating magnetic field when the at least one permanent magnet is positioned in the at least one section of the catheter tube, the longitudinal oscillations of the at least one permanent magnet producing longitudinal oscillations in the distal end portion of the guidewire.

16. The device according to claim 15, wherein the at least one permanent magnet is embedded in the guidewire.

17. The device according to claim 15, wherein the at least one permanent magnet is mounted on a surface of the guidewire.

18. The device according to claim 15, wherein the at least one electromagnetic coil is at least one of embedded in the catheter tube and mounted on a surface of the catheter tube such that a section of the guidewire passes through the at least one electromagnetic coil.

19. The device according to claim 15, wherein the at least one permanent magnet comprises a plurality of permanent magnets and wherein the at least one electromagnetic coil comprises a plurality of electromagnetic coils, the directions of the electrical currents in adjacent electromagnetic coils flowing in opposing directions, and the polarities of adjacent permanent magnets opposing each other.

20. The device according to claim 19, wherein the electromagnetic coils are powered independently by the electrical power source.

21. The device according to claim 15, wherein the at least one electromagnetic coil is electrically connected to an electrical power source by means of electrical wires, the electrical power source comprising means capable of measuring the ohmic resistance of the at least one electromagnetic coil in order to determine the temperature of the at least one electromagnetic coil.

* * * * *